US00PP16351P2

(12) United States Plant Patent
Li

(10) Patent No.: US PP16,351 P2
(45) Date of Patent: Mar. 21, 2006

(54) ***VERBENA* PLANT NAMED 'KLEVE03324'**

(50) Latin Name: *Verbena hybrida*
Varietal Denomination: Kleve03324

(75) Inventor: Ruijun Li, North Parramata (AU)

(73) Assignee: Klemm + Sohn GmbH + Company KG, Stuttgart (DE)

( * ) Notice: Subject to any disclaimer, the term of this patent is extended or adjusted under 35 U.S.C. 154(b) by 155 days.

(21) Appl. No.: 10/955,379

(22) Filed: Sep. 30, 2004

(51) Int. Cl.
*A01H 5/00* (2006.01)

(52) U.S. Cl. ..... Plt./308

(58) Field of Classification Search ..... Plt./308
See application file for complete search history.

*Primary Examiner*—Anne Marie Grunberg
(74) *Attorney, Agent, or Firm*—C. A. Whealy

(57) ABSTRACT

A new and distinct cultivar of *Verbena* plant named 'Kleve03324', characterized by its compact, upright, outwardly spreading and mounded plant habit; freely branching habit; dense and bushy growth habit; dark green-colored leaves; red-colored flowers with flowers held above and beyond the foliage; and resistance to Powdery Mildew.

1 Drawing Sheet

Botanical classification/cultivar designation: *Verbena hybrida* cultivar Kleve03324.

BACKGROUND OF THE INVENTION

The present Invention relates to a new and distinct cultivar of *Verbena* plant, botanically known as *Verbena hybrida*, and hereinafter referred to by the name 'Kleve03324'.

The new *Verbena* is a product of a planned breeding program conducted by the Inventor in Camden, New South Wales, Australia. The objective of the breeding program is to develop new compact *Verbena* cultivars with large flowrs and resistance to Powdery Mildew.

The new *Verbena* originated from a cross-pollination made by the Inventor in 2000 of a proprietary *Verbena hybrida* selection identified as 00.5.3, not patented, as the female, or seed, parent with a proprietary selection of *Verbena hybrida* identified as code number 00.10.4, not patented, as the male, or pollen, parent. The cultivar Kleve03324 was discovered and selected by the Inventor as a flowering plant within the progreny from this cross-pollination in a controlled environment in Camden, New South Wales, Australia in 2001.

Asexual reproduction of the new cultivar by terminal cuttings in a controlled environment in Camden, New South Wales, Australia since 2001, has shown that the unique features of this new *Verbena* are stable and reproduced true to type in successive generations of asexual reproduction.

SUMMARY OF THE INVENTION

The following traits have been repeatedly observed and are determined to be the unique characteristics of 'Kleve03324'. These characteristics in combination distinguish 'Kleve03324' as a new and distinct cultivar:

1. Compact, upright, outwardly spreading and mounded plant habit.
2. Freely branching habit; dense and bushy growth habit.
3. Dark green-colored leaves.

4. Red-colored flowers with flowers held above and beyond the foliage.
5. Resistant to Powdery Mildew.

Plants of the new *Verbena* differ primarily from plants of the parents in plant habit and flower coloration.

Plants of the new *Verbena* can be compared to plants of the cultivar Babylon Red, not patented. In side-by-side comparisons conducted in Camden, New South Wales, Australia, plants of the new *Verbena* differed from plants of the cultivar Babylon Red primarily in leaf shape as plants of the cultivar Babylon Red had deeply dissected leaves.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Verbena*. The photograph comprises a side perspective view of a typical flowering plant of 'Kleve03324' grown in a container.

DETAILED BOTANICAL DESCRIPTION

The cultivar Kleve03324 has not been observed under all possible environmental conditions. The phenotype may vary somewhat with variations in environment such as temperature and light intensity without, however, any variance in genotype. The aforementioned photographs and following observations and measurements describe plants grown in Stuttgart, Germany, under commercial practice during the spring in a glass-covered greenhouse with day temperatures about 18 to 22° C., night temperatures about 15 to 18° C. and light levels about 20,000 to 55,000 lux. Cuttings were planted in 12-cm containers and grown for about five months. In the following description, color references are made to The Royal Horticultural Society Colour Chart, 1995 Edition, except where general terms of ordinary dictionary significance are used.

Botanical classification: *Verbena hybrida* cultivar Kleve03324.

Parentage:

*Female, or seed, parent*.—Proprietary *Verbena hybrida* selection identified as 00.5.3, not patented.

*Male, or pollen, parent*.—Proprietary *Verbena hybrida* selection identified as code number 00.10.4, not patented.

Propagation:

*Type cutting*.—Terminal cuttings.

*Time to initiate roots, summer*.—About 5 to 8 days at 20° C.

*Time to initiate roots, winter*.—About 8 to 10 days at 20° C.

*Time to produce a rooted cutting or liner, summer*.—About 14 to 20 days at 20° C.

*Time to produce a rooted cutting or liner, winter*.—About 21 days at 20° C.

*Root description*.—Fine, fibrous; white in color.

*Rooting habit*.—Medium branching; moderately dense.

Plant description:

*Form*.—Compact, upright, outwardly spreading and mounded plant habit.

*Growth and branching habit*.—Moderately vigorous and freely-branching with lateral branches potentially developing at every node; dense and bushy growth habit.

*Plant height*.—About 15 to 20 cm.

*Plant diameter or spread*.—About 50 to 60 cm.

*Lateral branches*.—Length: About 15 to 30 cm. Diameter: About 2.5 mm. Internode length: About 2.5 to 7 cm. Texture: Slightly pubescent. Color: 137B.

*Foliage description*.—Arrangement: Opposite, simple. Length: About 3 to 5 cm. Width: About 1.5 to 3.5 cm. Shape: Roughly deltoid. Apex: Acute to rounded. Base: Attenuate. Margin: Crenate. Texture, upper and lower surfaces: Slightly pubescent. Venation pattern: Pinnate. Color: Developing foliage, upper surface: 137A. Developing foliage, lower surface: 137B. Fully expanded foliage, upper surface: 137B. Fully expanded foliage, lower surface: 137C. Venation, uper surface: 137B. Venation, lower surface: 137C. Petiole: Length: About 5 to 10 mm. Diameter: About 1 mm. Texture: Smooth. Color: 137B.

Flower description:

*Flower type and habit*.—Single upright salverform flowers arranged on compact terminal racemes; flowers sessile. Freely flowering with about 12 to 15 flowers per raceme. Inflorescences positioned above and beyond the foliage. Flowers last about one week under greenhouse conditions. Flowers not persistent.

*Fragrance*.—Faint.

*Flowering season*.—In the garden, flowering is continuous from spring until fall.

*Inflorescence height*.—About 3 to 6 cm.

*Inflorescence diameter*.—About 5 to 6 cm.

*Flower size*.—Diameter: About 2 cm. Depth: About 5 mm.

*Flower buds*.—Rate of opening, from showing color to fully open flower: About 1 to 2 days. Length: About 2 to 15 mm. Diameter: About 2 mm. Shape: Tubular, columnar. Color: 137B.

*Petals*.—Quantity/arrangement: Five per flower fused at base. Lobe length: About 5 to 15 mm. Lobe width: About 5 mm. Shape: Obovate. Apex: Rounded. Margin: Entire. Texture, upper and lower surfaces: Velvety, smooth. Color: When opening and fully opened, upper surface: 52A; color becoming closer to 53A with development. When opening and fully opened, lower surface: 52C.

*Sepals*.—Quantity/arrangement: Five, fused into a tube. Length: About 1 cm. Diameter: About 1 mm. Shape: Lanceolate. Apex: Acute. Base: Attenuate. Margin: Entire. Texture, upper and lower surfaces: Coarse, pubescent. Color, upper surface: 137B. Color, lower surface: 137C.

*Peduncles*.—Length: About 5 cm. Diameter: About 1.5 mm. Angle: Upright to about 45° from vertical. Strength: Strong. Color: Close to 137B.

*Reproductive organs*.—Stamens: Quantity per flower: Four; adnate to pistil. Anther shape: Elliptic. Anther length: About 1 mm. Anther color: 1C. Pollen amount: Scarce. Pollen color: 1C. Pistils: Quantity per flower: One. Pistil length: About 1.5 cm. Stigma shape: Spherical. Stigma color: 139C. Style length: About 1.5 cm. Style color: 139C. Ovary color: 139C.

*Fruit/seed*.—Fruit and seed production has not been observed.

Disease/pest resistance: Plants of the new *Verbena* have been observed to be resistant to Powdery Mildew. Plants of the new *Verbena* have not been observed to be resistant to pests and other pathogens common to *Verbena*.

Temperature tolerance: Plants of the new *Verbena* have been observed to be tolerant to temperatures ranging from 1 to 35° C.

It is claimed:

1. A new and distinct cultivar of *Verbena* plant named 'Kleve03324', as illustrated and described.

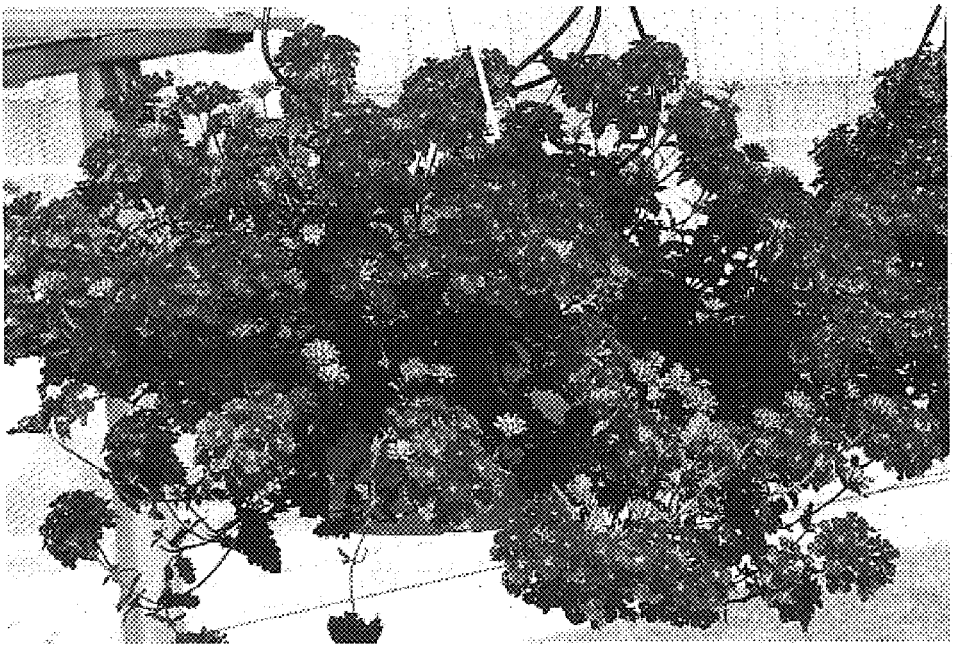

* * * * *